(12) United States Patent
Hirono

(10) Patent No.: US 7,295,306 B2
(45) Date of Patent: Nov. 13, 2007

(54) MICROCHIP AND FLUORESCENT PARTICLE COUNTER WITH MICROCHIP

(75) Inventor: Taisuke Hirono, Shizuoka (JP)

(73) Assignee: Kowa Company, Ltd., Aichi-ken (JP)

(*) Notice: Subject to any disclaimer, the term of this patent is extended or adjusted under 35 U.S.C. 154(b) by 284 days.

(21) Appl. No.: 11/106,776

(22) Filed: Apr. 15, 2005

(65) Prior Publication Data

US 2005/0237521 A1  Oct. 27, 2005

(30) Foreign Application Priority Data

Apr. 22, 2004  (JP) ............................. 2004-126516

(51) Int. Cl.
*G01N 1/10* (2006.01)
(52) U.S. Cl. .................................. 356/246
(58) Field of Classification Search ............... 356/317, 356/318, 417, 244–246, 39–42, 336–343, 356/432–436; 422/82.07; 702/21, 127
See application file for complete search history.

(56) References Cited

U.S. PATENT DOCUMENTS 5,247,340 A * 9/1993 Ogino ......................... 356/73
5,288,463 A * 2/1994 Chemelli ..................... 422/58
5,444,527 A * 8/1995 Kosaka ........................ 356/73
5,496,734 A * 3/1996 Sakata ......................... 436/63
5,500,187 A * 3/1996 Deoms et al. ................ 422/58
6,576,194 B1 * 6/2003 Holl et al. .................... 422/81
2002/0149766 A1 * 10/2002 Bardell et al. .............. 356/246

FOREIGN PATENT DOCUMENTS

JP  2001-083092 A  3/2001
JP  2002-221485 A  8/2002
JP  2003-181255     7/2003

* cited by examiner

*Primary Examiner*—Tarifur Chowdhury
*Assistant Examiner*—Jonathon D Cook
(74) *Attorney, Agent, or Firm*—Duane Morris LLP

(57) ABSTRACT

When connecting a blood collecting unit (not shown) with an adaptor, streaming blood in a first inflow passage, and streaming liquid including surfactant or fluorescent dyes in a second inflow passage, the blood and the liquid are mixed at a mixing portion, and platelets, erythrocytes and cell membranes of leukocytes in the blood are dissolved by the surfactant, and the nuclei of the leukocytes are fluorescently stained with the fluorescent dyes. Then, a fluorescent particle counting portion counts the fluorescently stained nuclei of the leukocytes during moving in an outflow passage. According to the invention, a number of leukocytes can be correctly measured with a simple operation, such as connection of a blood collecting unit or the like with the adaptor.

15 Claims, 7 Drawing Sheets

FIG. 3
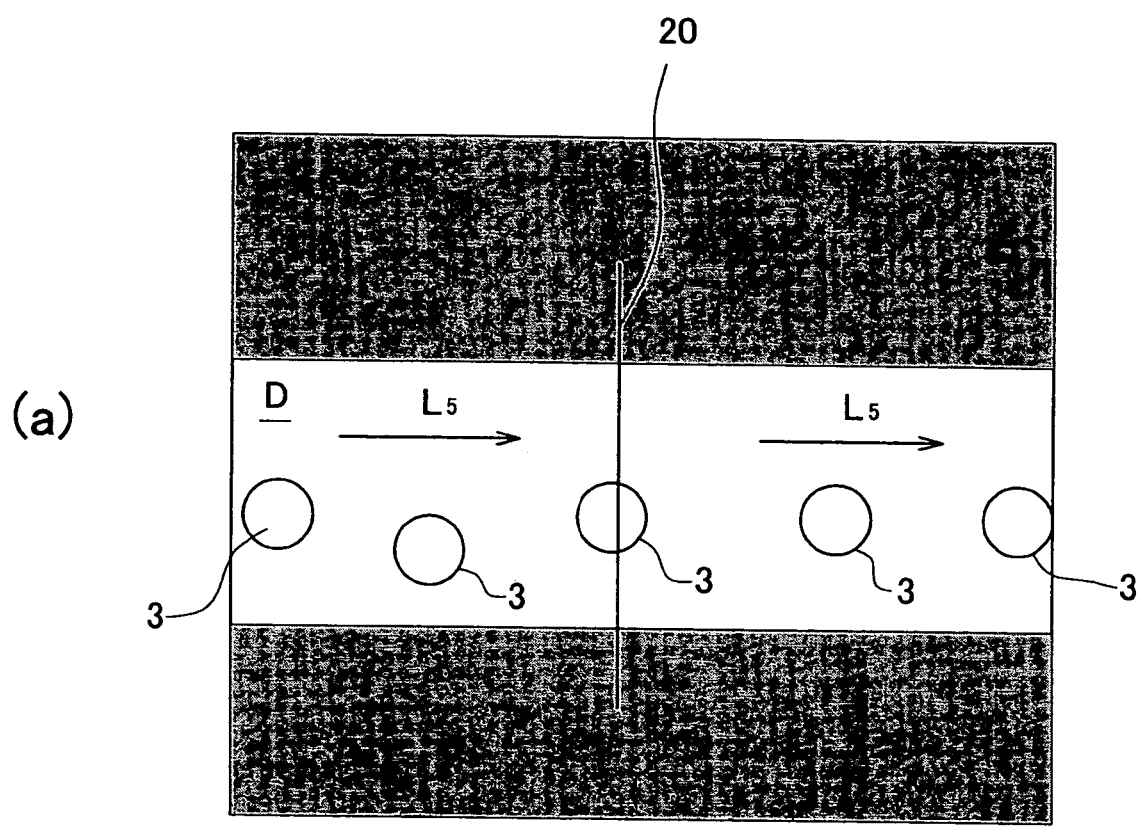
(a)
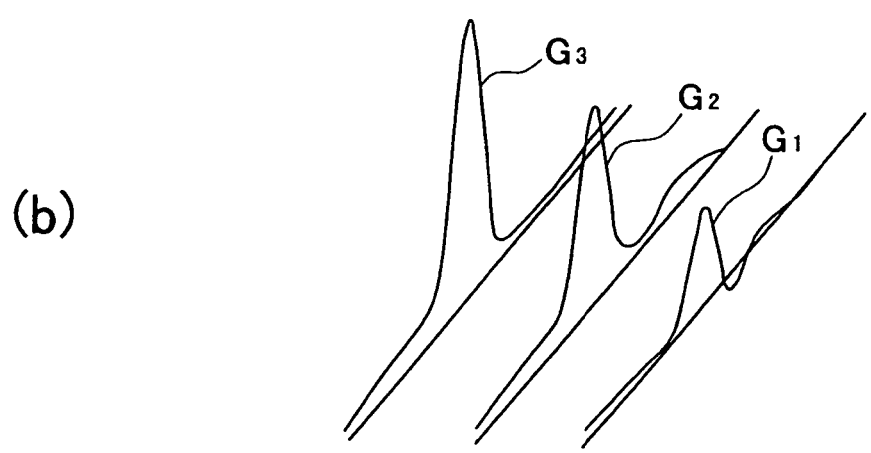
(b)

MICROCHIP AND FLUORESCENT PARTICLE COUNTER WITH MICROCHIP

BACKGROUND OF THE INVENTION

This invention relates to a microchip for mixing two or more liquid, and a fluorescent particle counter with the microchip.

In various technical fields, number of particles has been counted after fluorescently staining. In a medical field, for instance, platelet products and erythrocyte products which are made by respectively extracting platelets and erythrocytes from blood are used. It is preferable that no leukocyte remains in platelet products and erythrocyte products. For this reason, leukocytes are removed in a process of producing. In order to confirm whether or not leukocytes have been removed from a platelet product or an erythrocyte product, number of leukocytes is counted (see a Japanese patent application (Publication No. 2001-83092, for instance).

FIG. 4 is a block diagram showing a structure of a conventional leukocyte counter. A reference number 100 of FIG. 4 denotes a container for containing fluorescently stained platelet product and the like, and a reference number 101 denotes a laser beam source through which laser beam irradiates the container 100. A reference number 102 denotes a mirror, and a reference number 103 is a CCD camera. When laser beam (excitation light) irradiates the container 100 through the laser beam source 101 in such a counter, an image of leukocytes is obtained by the CCD camera 103. This image is captured in a computer (not shown) and is processed, and then, the number of the leukocytes is counted.

In order to fluorescently stain particles to be counted, it is necessary to mix fluorescent dyes into solution including particles. In order to fluorescently stain leukocytes in a platelet product, for instance, it is necessary to mix fluorescent dyes, such as propidium iodide, and a platelet product (concretely speaking, bare nuclei of leukocytes after platelets and erythrocytes are removed with surfactant, such as Triton X-100).

A machine for mixing two or more liquid (a microchip), which is not produced for a purpose of fluorescent particle counting, having a structure as shown in FIG. 5, has been proposed (see both Japanese patent applications (publication Nos. 2002-221485, 2003-181255), for instance). A reference number 200 in the figure denotes a specimen supply port for supplying liquid specimen, and a reference number 201 denotes a passage thereof. A reference number 202 denotes a reagent supply port for supplying liquid reagent, and a reference number 203 is a passage thereof. Specimen and reagent which are supplied through both supply ports 200, 202 meet together at a meeting portion 204 and are mixed, and drained from an exit 206 via an outflow passage 205.

In order to fluorescently stain particles, it is necessary to sufficiently mix fluorescent dyes into solution including particles. When fluorescently staining leukocytes with fluorescent dyes, for instance, propidium iodide or ethidium bromide, it is necessary to intercalate fluorescent dyes between bases of DNA of nuclei of leukocytes, and it is necessary to sufficiently mix. If particles are counted with a counting unit as shown in FIG. 4 after mixing fluorescent dyes with a structure as shown in FIG. 5, but, the counting accuracy of the particles is not good due to insufficient fluorescently staining. In order to remove platelets and erythrocytes and to obtain bare nuclei of leukocytes, it is necessary to sufficiently mix surfactant so as to react. But, in the structure as shown in FIG. 5, platelets and cell membranes of leukocytes remain due to insufficient mixing, so that the counting accuracy of leukocytes is made bad.

Besides, with the counting unit as shown in FIG. 4, an operation of entering of a fluorescently stained platelet product and the like into the container 10, a processing of rotation of the container 100 in order to fix fluorescent particles on a bottom of the container (centrifugation), and an operation of tracing (specifically determining) specimen in the container 100 are necessary, so that the counting operations are made complex.

Furthermore, it is necessary to switch an optical path according to concentration of specimen to be measured in case of the counting unit as shown in FIG. 4. For this reason, the counting operation is made more complex, and the structure of the unit is made complex.

Under these circumstances, a microchip for sufficiently mixing two or more liquid, and a fluorescent particle counter where a counting operation is simple have been desired.

SUMMARY OF THE INVENTION

The invention is a microchip, comprising:
a first inflow passage into which first liquid flows;
a second inflow passage into which second liquid flows;
a mixing portion connecting both said inflow passages, formed so as to be bent, for mixing said first liquid and said second liquid which flow therein; and
an outflow passage located so as to connect with said mixing portion, through which said mixed liquid is drained.

In this case, the mixing portion is formed so as to be bent, thereby sufficiently mixing the first and second liquid.

Besides, the invention is the microchip, wherein said mixing portion is almost zigzag bent.

In this case, the mixing portion is almost zigzag bent, thereby sufficiently mixing the first and second liquid. Besides, passage of the mixing portion takes a rather longer time, thereby sufficiently reacting the first and second liquid during the passage.

The invention is a fluorescent particle counter, comprising:
said microchip for mixing said first liquid including particles to be counted and said second liquid including fluorescent dyes in said mixing portion and for delivering fluorescent particles to said outflow passage;
a fluorescent particle counting portion for counting a number of said delivered fluorescent particles.

In this case, the first and second liquid can be sufficiently mixed so as to fluorescently stain the particles, and the fluorescent particle counting portion can correctly count the number of the fluorescent particles. Besides, the amount of the first and second liquid can be reduced by narrowing the inflow passage and the outflow passage of the microchip. Even if the first liquid is a platelet product or blood, vain loss of the platelet products can be restricted.

Besides, the invention is the fluorescent particle counter, further comprising a third inflow passage for supplying an upstream side of said mixing portion with diluent for diluting said first and second liquid.

In this case, diluent can dilute the first and second liquid, so that the fluorescent particles can be aligned in a thin layer, and the number of the fluorescent particles can be correctly counted even if the first and second liquid have high viscosity.

Besides, the invention is the fluorescent particle counter, further comprising a fourth inflow passage for supplying a downstream side of said mixing portion which is an upstream side of said outflow passage with fourth liquid so as to align said fluorescent particles by supplying said fourth liquid.

In this case, supply of the fourth liquid can align the fluorescent particles in a thin layer, so that the fluorescent particles can be correctly measured by the fluorescent particle counting portion in spite of concentrations of the first and second liquid. Then, it is not necessary to switch an optical passage according to the concentrations of liquid to be measured as disclosed in the Japanese patent application (Publication No. 2001-83092), thereby simplifying the counting operation or the unit. And, it is not necessary to align the fluorescent particles by centrifugation as the above-mentioned conventional unit, so that the counting operation can be simplified and the counting accuracy can be improved. And, error recognition of information due to human error can be eliminated, and physical and mental pains of an inspector can be reduced.

Besides, the invention is the fluorescent particle counter, wherein said fluorescent particle counting portion is comprised of a light source through which excitation light irradiates said fluorescent particles of said outflow passage, and a fluorescence measuring means for catching fluorescence which is generated due to irradiation of said excitation light onto said fluorescent particles.

In this case, the particles can be fluorescently stained by sufficiently mixing the first and second liquid, and the fluorescent particle counting portion can correctly count the number of the fluorescent particles. Besides, the amount of the first and second liquid can be reduced by narrowing the inflow passage and the outflow passage of the microchip. For instance, vain loss of platelet products can be restricted even if the first liquid is a platelet product or blood.

Besides, the invention is the fluorescent particle counter, wherein said first inflow passage is an inflow passage into which said first liquid including leukocytes flows, and said second inflow passage is an inflow passage into which said second liquid including surfactant for dissolving cell membranes of said leukocytes and said fluorescent dyes for fluorescently staining said leukocytes flows.

In this case, the platelets and the erythrocytes in the first liquid can be removed, and the cell membranes of leukocytes can be dissolved so as to fluorescently stain nuclei of the leukocytes, thereby correctly counting the leukocytes.

Besides, the invention is the fluorescent particle counter, wherein said first inflow passage has a connecting portion capable of attaching a blood collecting unit or a blood bag.

In this case, the number of the leukocytes can be counted only by connecting a blood collecting unit or a blood bag with the connecting portion, and it is not necessary to displace specimen for measurement to the other container as a conventional unit, thereby simplifying the counting operation. Besides, the number can be counted with the unit directly connecting with a blood collecting unit or a blood bag, so that it is not necessary to trace the information and then, error recognition of information due to human errors can be eliminated, and physical and mental pains of an inspector can be reduced.

Besides, the invention is the fluorescent particle counter, further comprising a sampling means for obtaining output of said fluorescence measuring means every constant time, and a counting means for counting a number of said fluorescent particles on the basis of said output of said sampling means.

In this case, it is possible to sufficiently mix the first and second liquid in order to fluorescently stain the particles, and it is possible to correctly count the fluorescent particles by the fluorescent particle counting portion. Besides, the amount of the first and second liquid can be reduced by narrowing the inflow passage and the outflow passage of the microchip. Even if the first liquid is a platelet product or blood, vain loss of the platelet products and the like can be restricted.

Besides, the invention is the fluorescent particle counter, wherein said fluorescent measuring means is a camera for obtaining stationary images in order every predetermined time.

In this case, a camera on the market can be used, thereby reducing the cost without necessitating production of a dedicated fluorescent measuring means.

Besides, the invention is the fluorescent particle counter, wherein said counting means counts a number of said fluorescent particles in a predetermined fluorescent distribution measurement area in each of said stationary images obtained by said fluorescence measuring means, and a width w of said predetermined fluorescent distribution measurement area in a direction where said fluorescent particles move meets the following expression width w of said predetermined fluorescent distribution measurement area is equal to moving speed of said fluorescent particles×time for said fluorescence measuring means from obtaining one said stationary image till obtaining the next image.

In this case, the number of the fluorescent particles is counted, making use of a constant virtual area. For this reason, the accuracy of counting can be improved in comparison with a case where the area is not used.

Besides, the invention is the fluorescent particle counter, wherein a width $w_x$ of the fluorescent distribution measurement area in the portion departing from a wall by x meets the following expression if a rate of flow of liquid flowing in said outflow passage changes between a portion adjacent to said wall and a central portion of said outflow passage width $w_x$ of said fluorescent distribution measurement area in the portion departing from said wall by x is equal to moving speed of said fluorescent particles in a point departing from said wall by x×time for said fluorescence measuring means from obtaining one said stationary image till obtaining the next stationary image.

In this case, the accuracy of counting of the fluorescent particles can be improved even if the rate of flow changes between the portion adjacent to the wall and the central portion of the outflow passage.

Besides, the invention is the fluorescent particle counter, wherein a side on an upstream side in said fluorescent distribution measurement area is a straight line intersecting said outflow passage, and a side on said downstream side in said area is a curved line projecting on said downstream side, and said area has a bullet-like shape.

In this case, the accuracy of counting of the fluorescent particles can be improved even if the rate of flow changes between the portion adjacent to the wall and the central portion of the outflow passage.

Besides, the invention is the fluorescent particle counter, said counting means counts any one of a fluorescent particle in a moment when passing through an edge on said upstream side in said fluorescent distribution measurement area and a fluorescent particle in a moment when passing through an edge on said downstream side in said fluorescent distribution measurement area in said stationary image, and does not count the other said fluorescent particle.

In this case, repeat counting is reduced so as to improve the accuracy of counting.

BRIEF DESCRIPTION OF THE DRAWINGS

FIG. 3(a) is a typical view for explaining a method of counting fluorescent particles, and FIG. 3(b) is a view showing a wave form of a fluorescent intensity distribution along a gate 20 of FIG. 3(a);

DESCRIPTION OF THE PREFERRED EMBODIMENTS

Best modes of embodiment for executing the invention are now explained, referring to FIG. 1 through FIG. 3 and FIGS. 6 and 7.

Figure 1:
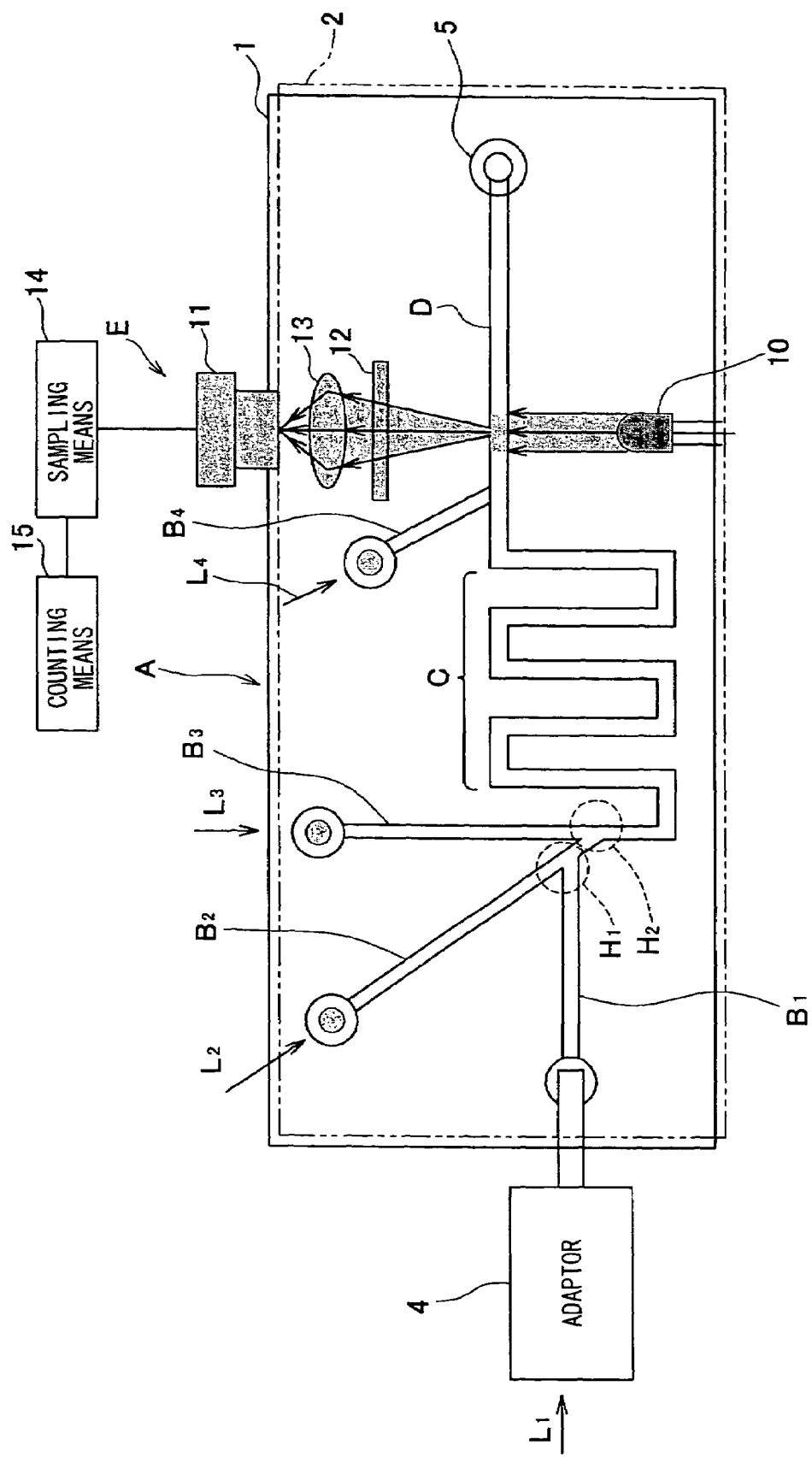
FIG. 1 is a typical view showing structures of a microchip and a fluorescent particle counter according to the invention.
Figure 2:
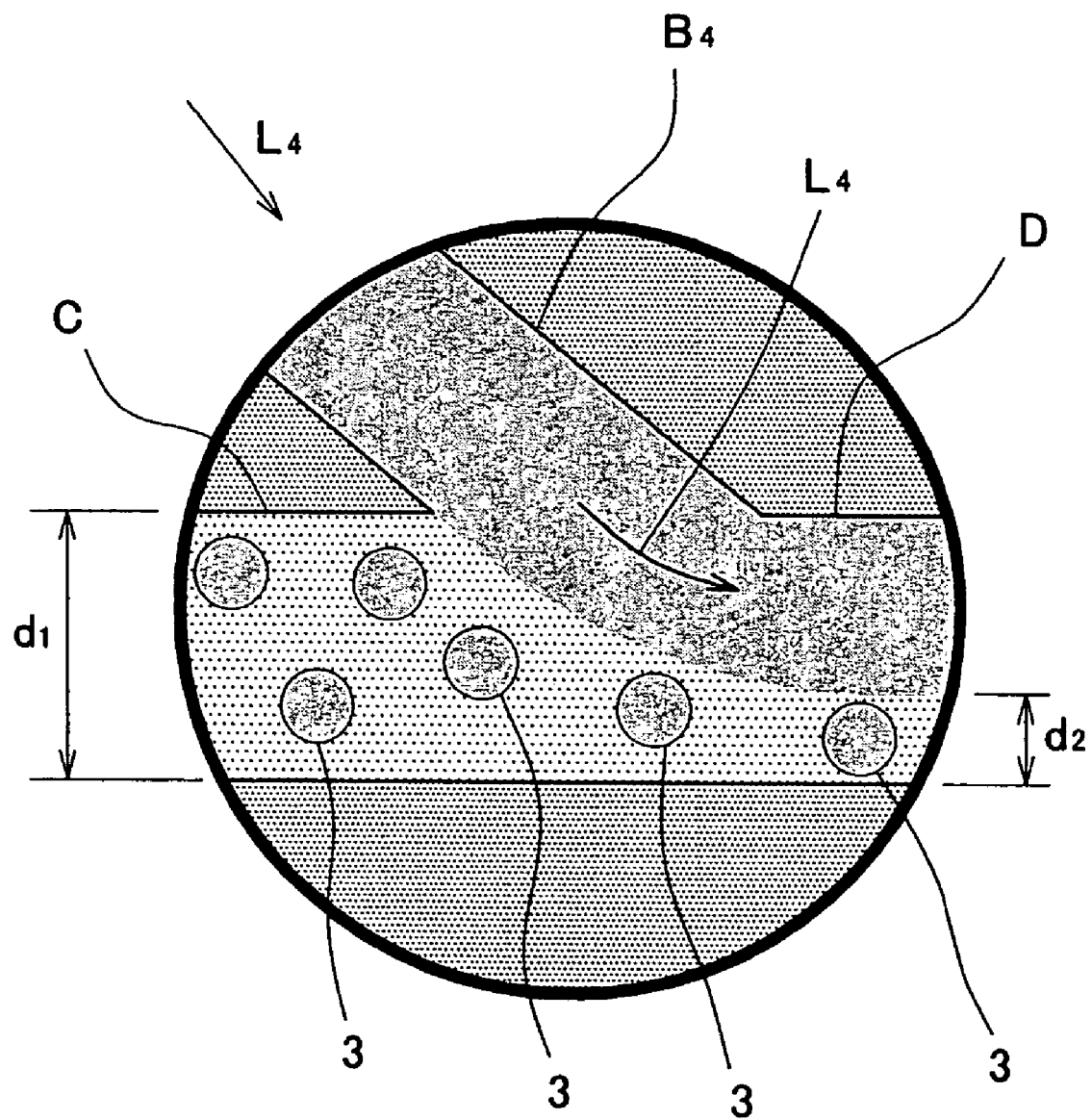
FIG. 2 is a typical view showing a way of aligning fluorescent particles through an inflow of fourth liquid.
Figure 6:
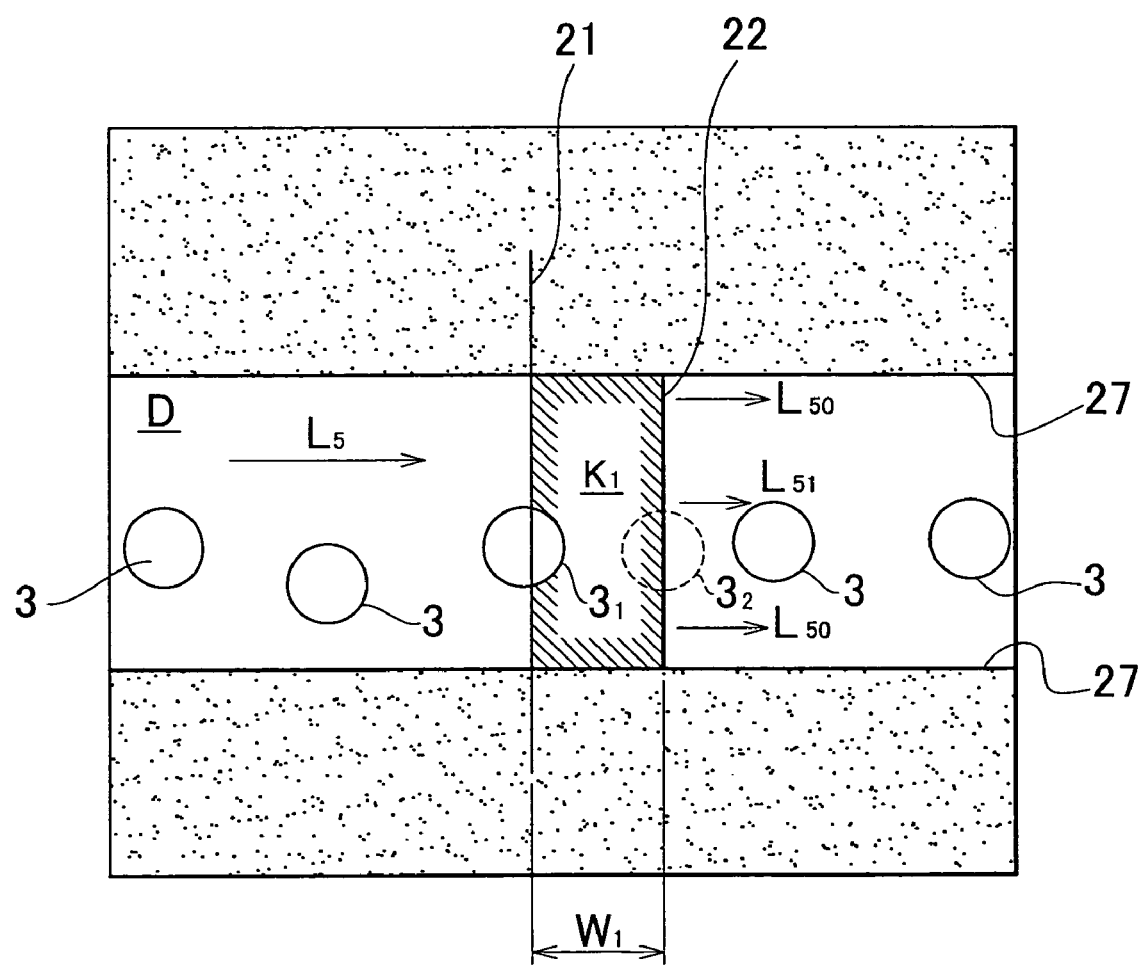
FIG. 6 is a typical view for explaining another method of counting fluorescent particles.
Figure 7:
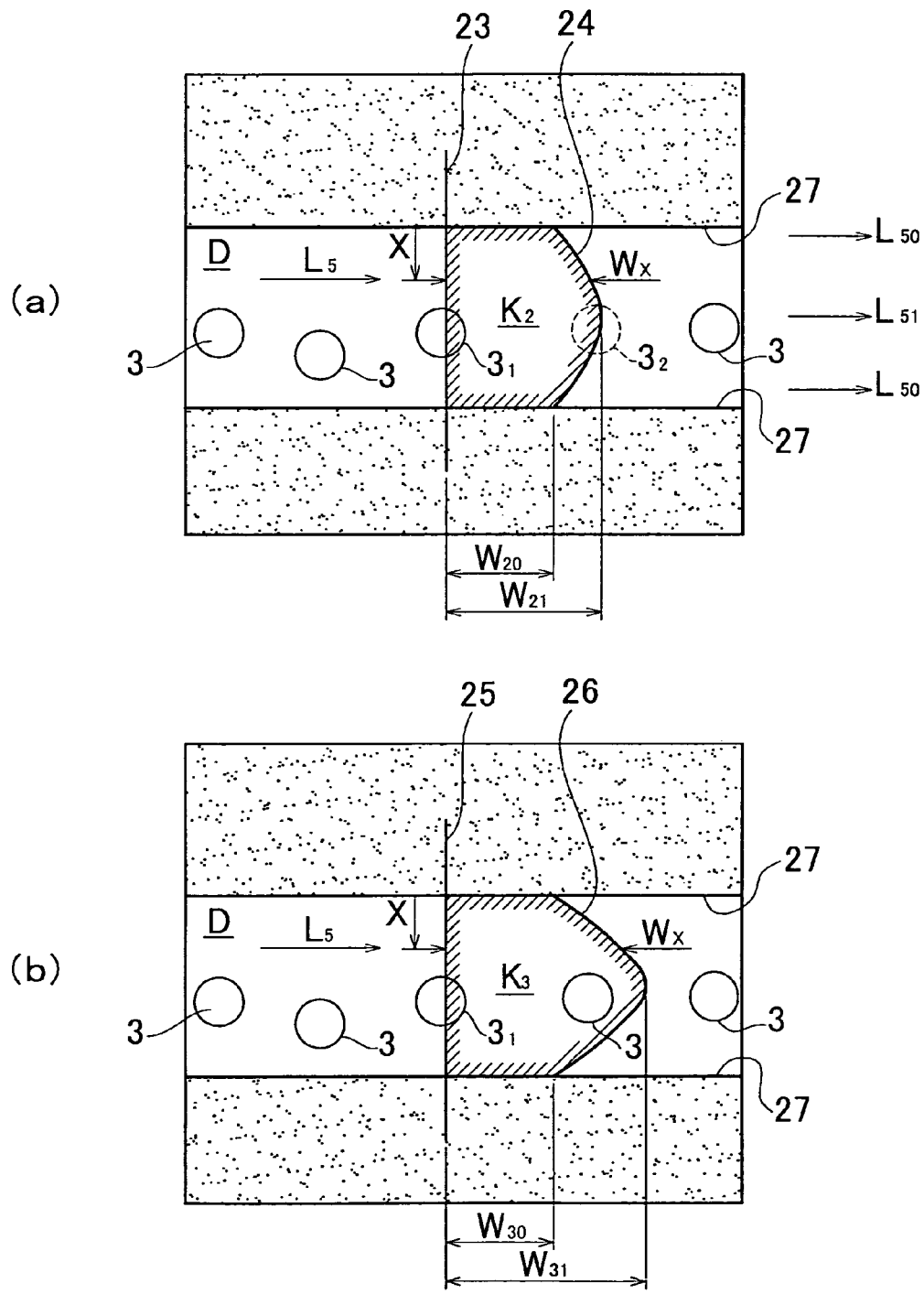
FIG. 7 is a typical view for explaining further another method of counting fluorescent particles.

FIG. 1 is a typical view showing structures of a microchip and a fluorescent particle counter according to the invention, FIG. 2 is a typical view showing a way of aligning fluorescent particles through an inflow of fourth liquid, FIG. 3(a) is a typical view for explaining a method of counting fluorescent particles, and FIG. 3(b) is a view showing a wave form of a fluorescent intensity distribution along a gate 20 of FIG. 3(a). And, FIG. 6 is a typical view for explaining another method of counting fluorescent particles, and FIG. 7 is a typical view for explaining further another method of counting fluorescent particles.

A microchip according to the invention depicted as A in FIG. 1 has a first inflow passage $B_1$ into which first liquid $L_1$ flows, a second inflow passage $B_2$ into which second liquid $L_2$ flows, a mixing portion C connecting with both inflow passages $B_1$, $B_2$, which is formed so as to be bent, for mixing the first liquid $L_1$ and the second liquid $L_2$ which flows therein, and an outflow passage D located so as to connect with the mixing portion C, through which the mixed liquid is drained. According to the invention, the mixing portion C is formed so as to be bent, thereby sufficiently mixing the first and second liquid $L_1$, $L_2$.

Preferably, the mixing portion C is almost zigzag bent so as to sufficiently mix the first and second liquid $L_1$, $L_2$. By doing so, it is possible to sufficiently mix the first and second liquid $L_1$, $L_2$. Besides, passing through the mixing portion C takes a rather longer time, so that it is possible that the first and second liquid $L_1$, $L_2$ sufficiently react during the passage. A surfactant described hereinafter, for instance, can sufficiently dissolve cell membranes of leukocytes, erythrocytes, and platelets.

Each of the inflow passages $B_1$, $B_2$, the mixing portion C and the outflow passage D may be formed in the shape of a groove on a surface of a base plate 1, and a cover member 2 may be attached to the surface.

And, the fluorescent particle counter according to the invention has the microchip A having the above-mentioned structure. Preferably, specimen for measurement including particles (such as leukocytes) to be counted (such as blood, a platelet product and an erythrocyte product) as the first liquid $L_1$ flows in the first inflow passage $B_1$ of the microchip A, and solution including fluorescent dyes as the second liquid $L_2$ flows in the second inflow passage $B_2$. In such a case, the first and second liquid $L_1$, $L_2$ are mixed at the mixing portion C, and fluorescent particles are formed (see reference number 3 of FIG. 2) and delivered to the outflow passage D. Thereafter, the delivered fluorescent particles 3 may be counted by a fluorescent particle counting portion depicted as E of FIG. 1. According to this fluorescent particle counter, the particles can be fluorescently stained by sufficiently mixing the first and second liquid $L_1$, $L_2$ so as to correctly count the number of the fluorescent particles 3 by the fluorescent particle counting portion E. And, the inflow passages $B_1$, $B_2$ and the outflow passage D of the microchip A can be narrowed so as to reduce the amount of the first and second liquid $L_1$, $L_2$. Even if the first liquid $L_1$ is a platelet product or blood, vain loss of platelet products and the like can be saved.

When counting the number of leukocytes in a platelet product or an erythrocyte product, it is necessary to remove platelets and erythrocytes, and to make bare nuclei of leukocytes (to remove cell membranes of leukocytes). In order to do so, it is preferable to add surfactant for dissolving cell membranes of leukocytes, platelets and erythrocytes to the first liquid $L_1$, (the above-mentioned product) or the second liquid $L_2$ (solution including fluorescent dyes) so as to be mixed. The first inflow passage $B_1$ may be an inflow passage into which the first liquid $L_1$ including leukocytes flows, and the second inflow passage $B_2$ may be an inflow passage into which the second liquid $L_2$ including surfactant for dissolving cell membranes of leukocytes and fluorescent dyes for fluorescently staining leukocytes flows. In such a case, platelets and erythrocytes can be removed, and the cell membranes of leukocytes can be dissolved so as to fluorescently stain cell membranes of leukocytes, thereby correctly counting leukocytes. The surfactant may be TritonX-100, and the fluorescent dyes may be propidium iodide or ethidium bromide.

The number of the second inflow passage $B_2$ as shown in FIG. 1 is only one, but two or more second inflow passages $B_2$ may be provided so that surfactant and fluorescent dyes can be supplied through respectively different inflow passages $B_2$.

Preferably, a third inflow passage $B_3$ is provided on an upstream side rather than the mixing portion C so as to supply the upstream side of the mixing portion C with diluent (third liquid) $L_3$ for diluting the first liquid $L_1$ and the second liquid $L_2$. In such a case, the first liquid $L_1$ and the second liquid $L_2$ can be diluted, so that fluorescent particles can be aligned in thin layer, and can be correctly counted even if the first liquid $L_1$ and the second liquid $L_2$ have high viscosity (such as, blood having inclination of hyperlipemia, viscosity of which is high and chylous blood). Preferably, the diluent may be transparent buffer having no color, through which cells can stably exist. Concretely speaking, it is PBS buffer, preferably. Before streaming the first liquid $L_1$ into the first inflow passage $B_1$ or streaming the second liquid $L_2$ into the second inflow passage $B_2$, the first liquid $L_1$ or the second liquid $L_2$ may be diluted so as to have a proper viscosity (the viscosity with which at least both liquid $L_1$, $L_2$ can smoothly flow in the inflow passages $B_1$, $B_2$) in advance, and thereafter, diluent is streamed from the third inflow passage $B_3$ also so that the liquid may have the most optimum viscosity (such as, the most optimum viscosity with which the fluorescent particles flows, respectively separated from each other). For instance, the first liquid $L_1$ may be adjusted by mixing diluent in blood having high viscosity in order to have proper viscosity, the adjusted first liquid $L_1$ may be streamed into the first inflow passage $B_1$, and subsequently, fluorescent dyes is mixed from the second inflow passage $B_2$ so as to fluorescent stain leukocytes, and thereafter, diluent may be streamed from the third inflow passage $B_3$ so as to finally adjust the viscosity. In FIG. 1, the third inflow passage $B_3$ meets the first and second inflow passages $B_1$ and $B_2$ on a downstream side (see $H_2$) rather than a meeting portion $H_1$ between the first and second inflow passages $B_1$ and $B_2$ (That is, with this structure, the diluent $L_3$ is mixed after mixing the first and second liquid $L_1$, $L_2$). Alternatively, a meeting portion between the first and third inflow passages $B_1$ and $B_3$ is provided on an upstream side rather than a point meeting the second inflow passage $B_2$ such that the first liquid $L_1$ and the diluent L3 are mixed, and then the second liquid $L_2$ is mixed therein, or a meeting portion between the second and third inflow passages $B_2$ and $B_3$ is provided on an upstream side rather than a point meeting the first inflow passage $B_1$ such that the second liquid $L_2$ and the diluent $L_3$ are mixed, and then the first liquid $L_1$ is mixed therein.

When the particles 3 connecting each other (a lump of particles 3) pass through the fluorescent particle counting portion E, two or more particles 3 are counted as one particle, so that the counting accuracy is made lower. For this reason, it is necessary that the particles 3 pass through the fluorescent particle counting portion E, departing from each other (separating from each other) Preferably, the fluorescent particle counting portion E or the other means detects whether or not the fluorescent particles 3 are connected with each other, and the detected information is feedbacked to means for streaming diluent into the third inflow passage $B_3$ (diluent streaming means) or means for streaming fourth liquid $L_4$ (described hereinafter in detail), and the amount of the diluent or the fourth liquid $L_4$ to be streamed is adjusted according to the state of the fluorescent particles 3 such that the fluorescent particles 3 can be delivered, respectively separated from each other.

Besides, preferably, a fourth inflow passage $B_4$ for supplying the fourth liquid $L_4$ is provided on a downstream side of the mixing portion C on an upstream side of the outflow passage D, and the fourth liquid $L_4$ is supplied so as not to disturb flow from the mixing portion C (flow having some layers) so that the fluorescent particles 3 can be aligned (see FIG. 2). The fourth liquid $L_4$ may be the above-mentioned buffer. Preferably, in this case, a flow having some layers from the mixing portion C is narrowed (see $d_1$ and $d_2$) by adjusting a streaming direction or a streaming speed of the fourth liquid $L_4$, so that the fluorescent particles 3 can flow in only one layer of flow along a wall face of the outflow passage D. In such a case, the fluorescent particle counting portion E can correctly measure the fluorescent particles 3 in spite of concentrations of the first and second liquid $L_1$, $L_2$. That is, it is not necessary to switch an optical passage according to light absorption characteristics or optical characteristics of liquid to be measured as disclosed in the Japanese patent application (Publication No. 2001-83092), thereby simplifying the counting operation or the unit. That is, a thickness of the layer where the fluorescent particles 3 exist in the outflow passage D (the thickness in a direction where a light source 10 radiates) is thin enough to obtain images with a camera, so that a difference of transmissivity of a platelet product and a whole blood/erythrocyte product can be extremely prevented from giving an influence on amount of fluorescence as background light which is excited from the fluorescent dyes remaining in liquid. Then, it is not necessary to switch the optical path from the light source to the outflow passage D in order to prevent the influence of the background light. Besides, it is not necessary to align the fluorescent particles by centrifugation as a conventional unit, so that the counting operation can be simplified (physical and mental pains of an inspector can be reduced), and the counting accuracy can be improved. And, error recognition of information due to human error can be eliminated, thereby reducing physical and mental pains of an inspector. When using an optical system having deep depth of focus, it is not necessary to align nuclei of leukocytes, so that the passage pattern more simple than one as shown in FIG. 1 can be adopted.

Figure 4:
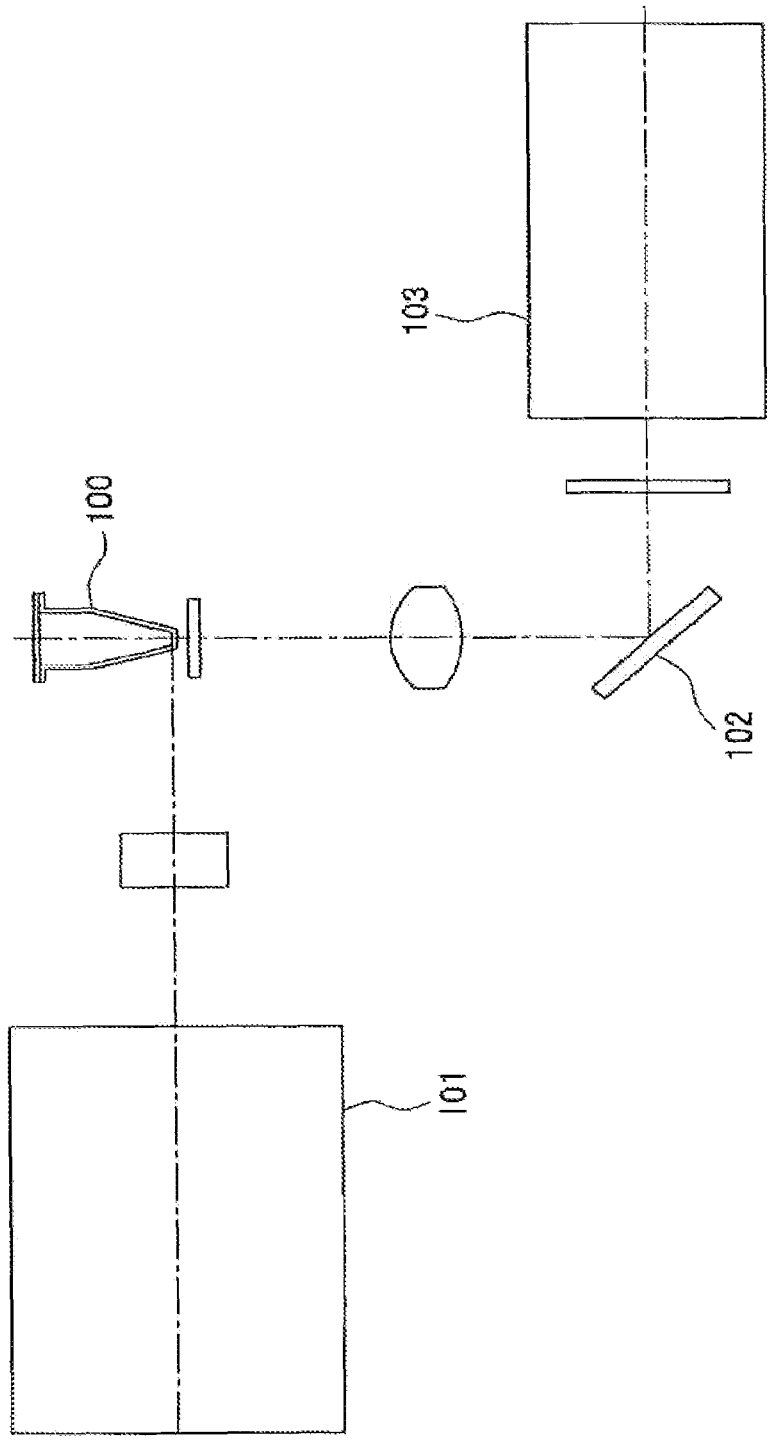
FIG. 4 is a block diagram showing a structure of a conventional leukocyte counter.
Figure 5:
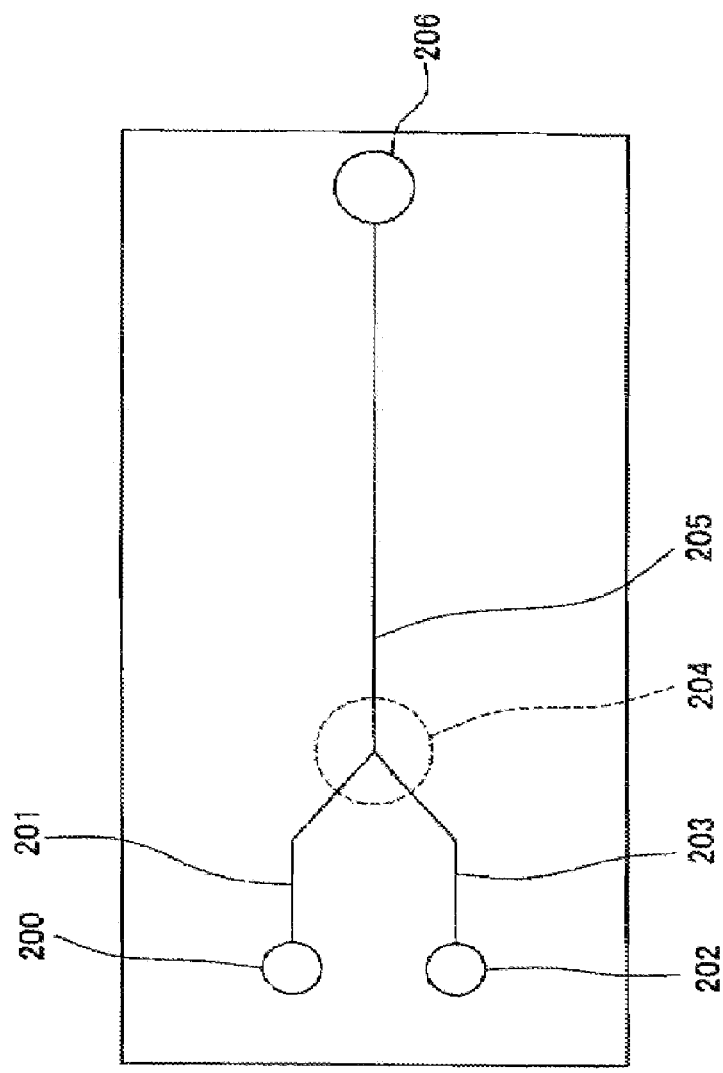
FIG. 5 is a typical view showing a structure of a conventional unit for mixing two or more liquid.

Preferably, the first inflow passage $B_1$ is provided with a connecting portion (adaptor) 4 for installing a blood collecting unit or a blood bag. In such a case, the number of leukocytes can be counted by only connecting a blood collecting unit or a blood bag with the connecting portion 4, and it is not necessary to displace the specimen for measurement to a different container (such as the container 100 of FIG. 4) as a conventional unit, thereby simplifying the counting operation (reducing physical and mental pains of an inspector). When the number of leukocytes exceeds a standard, the leukocytes may be reduced with a leukocyte removing filter or the like. It is easy to test all of collected blood and to increase a number of sampling inspection since the counting operation is made simplified. When testing all of the collected blood and increasing a number of sampling inspection, off-spec products can be more certainly prevented to be produced in comparison with a case where a number of sampling inspection is small. Furthermore, the number of leukocytes can be counted with a unit directly connecting with a blood collecting unit or a blood bag, so that it is not necessary to trace the information (although in a case with the container 100 as shown in FIG. 4, it is necessary to specifically determine which specimen is in each container 100, in a case where a blood collecting unit or the like is directly connected with the counting unit, such an specifically determining operation is not necessary). Then, error recognition of information due to human error can be eliminated, and physical and mental pains of an inspector can be reduced.

Preferably, an opening portion (output port) 5 is provided at the outflow passage D so that the first and second liquid $L_1$, $L_2$ can flow in layers in the respective inflow passages, by sucking through the opening portion 5.

Preferably, the fluorescent particle counting portion E is comprised of the light source 10 through which excitation light irradiates the fluorescent particles 3 of the outflow passage D, and a fluorescence measuring means 11 for obtaining (measuring) fluorescence generated by the irradiation of the excitation light onto the fluorescent particles 3.

It is necessary to select the light source 10 so as to correspond to light absorption characteristics of the fluorescent dyes (dyes for fluorescently staining particles of leukocytes). When using propidium iodide (PI) as the fluorescent dyes, the light source for generating green light (the excitation light, wavelength area of which is about 500 through 550 nm) is preferable. When using ethidium bromide (EtBr) as the fluorescent dyes, the light source for generating ultraviolet light is preferable.

And, a camera for obtaining stationary images in order every predetermined time can be used as the fluorescence measuring means 11. Concretely speaking, such camera is a video camera, a CCD camera and a USB camera. In this case, a camera on the market can be used, thereby reducing the cost without necessitating production of a dedicated fluorescent measuring means.

Preferably, an optical filter 12 for passing through only light generated due to fluorescence (light having the other wavelength area can not be passed through) or a lens 13 for converging is provided between the fluorescence measuring means 11 and the outflow passage D.

Preferably, a sampling means 14 is connected with the fluorescence measuring means 11 so as to obtain output of the fluorescence measuring means 11 every constant time. Besides, preferably, a counting means 15 is connected with the sampling means 14 so as to count the number of the fluorescent particles 3 on the basis of the output of the sampling means 14. That is, the gate 20 which intersects the outflow passage D where the fluorescent particles 3 move as shown with an arrow $L_5$ in FIG. 3(a) is virtually provided, and one dimensional fluorescent intensity distribution along the gate 20 is obtained by the fluorescence measuring means 11 and the sampling means 14. In the result, one dimensional fluorescent intensity distribution G1, G2, G3 . . . is obtained every constant time as shown in FIG. 3(b). Then, the counting means 15 analyzes such a fluorescent intensity distribution so as to count the fluorescent particles 3 which pass through the gate 20. When taking moving images at 30 fps of video rate with a camera having the fluorescence measuring means 11 and the sampling means 14, stationary images can be obtained every 1/30 second, through which the fluorescent intensity distribution as shown in FIG. 3(b) can be obtained. Preferably, the number of the fluorescent particles 3 is counted by analyzing the obtained fluorescent intensity distribution. Alternatively, the number of the fluorescent particles 3 may be counted by catching objects appearing in the moving images with a movement detecting technique to be used in compression/analysis technique of moving images.

When counting the number of fluorescent particles 3 on the basis of the above-mentioned one-dimensional fluorescent intensity distribution measurement, it is necessary to obtain an image of all fluorescent particles 3 in a moment when passing through the gate 20 only once with a camera. This is because if some fluorescent particles flow without obtaining the image thereof at a moment when passing through the gate, the number of the fluorescent particles can not counted, so that the accuracy of counting is made worse. On the contrary, if the image of some fluorescent particles at a moment when passing through the gate 20 is obtained twice or more due to a short image obtaining interval with a camera (time from obtaining one stationary image by a camera till obtaining the next stationary image, as mentioned hereinafter), the number of the fluorescent particles are repeatedly counted, so that the accuracy of counting is also made worse. In order to obtain an image of all fluorescent particles 3 at a moment when passing through the gate 20 only once with a camera, it is necessary to optimally adjust a relation between a video rate of a video camera and a rate of flow (the rate of flow of liquid flowing in the outflow passage D as shown with $L_5$ of FIG. 3(a)).

If a counting error of the fluorescent particles is difficult to be avoided in the above-mentioned one-dimensional fluorescent intensity distribution measurement, the counting means 15 may count the number of the fluorescent particles in a predetermined fluorescent distribution measurement area in each stationary image which was obtained by the fluorescence measuring means 11. Preferably, a width w of the predetermined fluorescent distribution measurement area (length in a direction where the fluorescent particles move) meets the following expression.

> width w of the predetermined fluorescent distribution area is equal to moving speed of fluorescent particles×time for the fluorescence measuring means from obtaining one stationary image till obtaining the next stationary image ("the image obtaining interval" hereinafter)

In such a case, the number of the fluorescent particles is counted, making use of a constant virtual area. For this reason, the counting error can be reduced so as to improve the accuracy of counting in comparison with a case where the area is not used.

For instance, such fluorescent distribution measurement area is a two-dimensional rectangular area $K_1$ as shown with oblique lines of FIG. 6. Width $w_1$ of the area may be obtained by the following expression.

> width $w_1$ of the rectangular area $K_1$ is equal to rate of flow $L_5$ of liquid flowing in the outflow passage D×the image obtaining interval When thus setting the width $w_1$ of the rectangular area $K_1$, the image of all the fluorescent particles flowing in the outflow passage is theoretically obtained once in the area $K_1$ in any stationary image, thereby reducing the counting error of the fluorescent particles, such as failing to count and repeat counting, and improving the accuracy of counting. But, as shown in FIG. 6, the fluorescent particle $3_1$ the image of which was obtained at a moment passing through a side (an edge) 21 on the upstream side of the rectangular area $K_1$, only the right half thereof entering the rectangular area $K_1$ moves $w_1$ in the next image obtaining timing so as to be located at a position $3_2$, so that the image is finally obtained twice. As the result, both are counted, so that the accuracy of counting is made worse. Preferably, the counting means 15 does not count both the fluorescent particle (such as the fluorescent particle $3_1$) in a moment passing through a side 21 on the upstream side of the rectangular area (the fluorescent distribution measurement area) $K_1$ and the fluorescent particle (such as the fluorescent particle $3_2$) in a moment passing through a side (an edge) 22 on the downstream side of the rectangular area $K_1$ in all stationary images obtained, only any one of both is counted, but the other is not counted. By doing so, repeat counting is reduced so as to improve the accuracy of counting.

The method as shown in FIG. 6 is effective if the rates of flows in a central portion and in a portion adjacent to a wall of the outflow passage D (see $L_{51}$ and $L_{50}$ of FIG. 6) are almost the same, but in many cases, both rates of flows are different from each other. When streaming liquid in the outflow passage D at a slightly high speed, the rate of flow is made slower in the portion adjacent to a wall 27 due to an influence received from the wall 27, and then, the rate of flow $L_{51}$ in the central portion of the outflow passage D is made finally faster than the rate of flow $L_{50}$ in the portion adjacent to the wall, so that big difference between both occurs. In such a case (if the rate of flow of liquid which flows in the outflow passage D changes between the portion adjacent to the wall and the central portion in the outflow passage D), the fluorescent distribution measurement area may not be one in the shape of a rectangle having a constant width $w_1$ as shown in FIG. 6, but may be one having the area width in the central portion (see $w_{21}$) of the outflow passage D which is wider than the area width in the portion adjacent to the wall (see $w_{20}$), as shown in FIG. 7(a). And, preferably, the width $w_x$ of the fluorescent distribution measurement area in the portion departing from the wall 27 of the outflow passage D by x meets the following expression.

> width $w_x$ of the fluorescent distribution measurement area in the portion departing from the wall by x=moving speed of the fluorescent particles in a
point departing from the wall by x×the image
obtaining interval In such a case, the accuracy of counting of the fluorescent particles can be improved even if the rate of flow changes between the portion adjacent to the wall and the central portion of the outflow passage D.

Concretely speaking, the following expressions are used.

area width $w_{21}$ in the central portion in the outflow
passage D is equal to rate of flow $L_{51}$ in the
central portion×the image obtaining interval area width $w_{20}$ in the portion adjacent to the wall is
equal to rate of flow $L_{50}$ in the portion adjacent
to the wall×the image obtaining interval If the difference between the rate of flow $L_{51}$ in the central portion of the outflow passage D and the rate of flow $L_{50}$ in the portion adjacent to the wall is big, preferably, the area width (see $w_{31}$) in the central portion of the outflow passage D is set to be extremely broader than the area width (see $w_{30}$) in the portion adjacent to the wall, as shown in FIG. 7(b).

In the area $K_2$ as shown in FIG. 7(a) also, the fluorescent particle $3_1$ the image of which was obtained in a moment passing through a side (an edge) 23 on the upstream side of the area $K_2$, the right half thereof entering the area $K_2$, positions at $3_2$ in the next image obtaining timing, so that the image is finally obtained twice. As the result, both are counted, so that the accuracy of counting is made worse. Preferably, the counting means 15 does not count both the fluorescent particle (such as the fluorescent particle $3_1$) in a moment passing through a side 23 on the upstream side of the area $K_2$ and the fluorescent particle (such as the fluorescent particle $3_2$) in a moment passing through an edge (boundary) 24 on the downstream side of the area $K_2$ in all stationary images obtained, only any one of both is counted, but the other is not counted. By doing so, repeat counting is reduced so as to improve the accuracy of counting.

Each of the areas $K_2$, $K_3$ in FIG. 7(a),(b), has the side 23 or 25 on the upstream side which is a straight line intersecting the outflow passage D and the side 24 or 26 on the downstream side which is a curved line projecting on the downstream side so as to have bullet-like shape (in other expression, home-like shape in baseball). Preferably, the sides 23, 25 on the upstream side are straight lines since it is easy to count the fluorescent particles in a moment when passing through the sides 23, 25. If the area widths $w_{20}$, $w_{21}$ meet the above-mentioned expressions, the edges on the upstream side may not be straight lines, but curved lines.

The present invention has been explained on the basis of the example embodiments discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. A fluorescent particle counter comprising:
a microchip being comprised of a first inflow passage into which first liquid flows, a second inflow passage into which second liquid flows, a mixing portion connecting both said inflow passages, formed so as to be bent for mixing said first liquid said second liquid which flow therein, and an outflow passage located so as to connect with said mixing portion, through which said mixed liquid is drained;
said microchip for mixing said first liquid including particles to be counted and said second liquid including fluorescent dyes in said mixing portion and for delivering fluorescent particles to said outflow passage;
a fluorescent particle counting portion being comprised of a light source through which excitation light irradiates said fluorescent particles of said outflow passage, and a fluorescence measuring means for catching fluorescence which is generated due to irradiation of said excitation light onto said fluorescent particles so as to counter said delivered fluorescent particles;
a sampling means for obtaining output of said fluorescence measuring means every constant time, and a counting means for counting a number of said fluorescent particles on the basis of said output of said sampling means;
said fluorescent measuring means being a camera for obtaining stationary images in order every predetermined time;
wherein said counting means counts a number of said fluorescent particles in a predetermined fluorescent distribution measurement area in each of said stationary images obtained by said fluorescence measuring means, and a width w of said predetermined fluorescent distribution measurement area in a direction where said fluorescent particles move meets the following expression
width w of said predetermined fluorescent distribution measurement area is equal to moving speed of said fluorescent particles×time for said fluorescence measuring means from obtaining one said stationary image till obtaining the next image.

2. The microchip according to claim 1, wherein said mixing portion is almost zigzag bent.

3. The fluorescent particle counter according to claim 1, further comprising a third inflow passage for supplying an upstream side of said mixing portion with diluent for diluting said first and second liquid.

4. The fluorescent particle counter according to claim 1, further comprising a fourth inflow passage for supplying a downstream side of said mixing portion which is an upstream side of said outflow passage with fourth liquid so as to align said fluorescent particles by supplying said fourth liquid.

5. The fluorescent particle counter according to claim 1, wherein said first inflow passage is an inflow passage into which said first liquid including leukocytes flows, and said second inflow passage is an inflow passage into which said second liquid including surfactant for dissolving cell membranes of said leukocytes and said fluorescent dyes for fluorescently staining said leukocytes flow.

6. The fluorescent particle counter according to claim 5, wherein said first inflow passage has a connecting portion capable of attaching a blood collecting unit or a blood bag.

7. The fluorescent particle counter according to claim 1, wherein a width $w_x$ of said fluorescent distribution measurement area in the portion departing from a wall by x meets the following expression if a rate of flow of liquid flowing in said outflow passage changes between a portion adjacent to said wall and a central portion of said outflow passage
width $w_x$ of said fluorescent distribution measurement area in said portion departing from said wall by x is equal to moving speed of said fluorescent particles in a point departing from said wall by x×time for said fluorescence measuring means from obtaining one said stationary image till obtaining the next stationary image.

8. The fluorescent particle counter according to claim 7, wherein a side on an upstream side in said fluorescent distribution measurement area is a straight line intersecting said outflow passage, and a side on said downstream side in said area is a curved line projecting on said downstream side, and said area has a bullet-like shape.

9. The fluorescent particle counter according to claim 1, said counting means counts any one of a fluorescent particle in a moment when passing through an edge on said upstream side in said fluorescent distribution measurement area and a fluorescent particle in a moment when passing through an edge on said downstream side in said fluorescent distribution measurement area in said stationary image, and does not count the other said fluorescent particle.

10. A fluorescent particle counter comprising:
a microchip being comprised of a first inflow passage into which first liquid flows, a second inflow passage into which second liquid flows, a mixing portion connecting both said inflow passages, formed so as to be bent, for mixing said first liquid and said second liquid which flow therein, and an outflow passage located so as to connect with said mixing portion, through which said mixed liquid is drained;
said microchip for mixing said first liquid including particles to be counted and said second liquid including fluorescent dyes in said mixing portion and for delivering fluorescent particles to said outflow passage;
a fluorescent particle counting portion is comprised of a light source through which excitation light irradiates said fluorescent particles of said outflow passage, and a fluorescence measuring unit for catching fluorescence which is generated due to irradiation of said excitation light onto said fluorescent particles;
a sampling unit for obtaining output of said fluorescence measuring unit every constant time, and a counting unit for counting a number of said fluorescent particles on the basis of said output of said sampling unit; and
said fluorescent measuring unit is a camera for obtaining stationary images in order every predetermined time;
wherein said counting unit counts a number of said fluorescent particles in a predetermined fluorescent distribution measurement area in each of said stationary images obtained by said fluorescence measuring unit and a width w of said predetermined fluorescent distribution measurement area in a direction where said fluorescent particles move meets the following expression
width w of said predetermined fluorescent distribution area is equal to moving speed of said fluorescent particles×time for said fluorescence measuring unit from obtaining one said stationary image till obtaining the next image.

11. The fluorescent particle counter according to claim 10, wherein said first inflow passage is an inflow passage into which said first liquid including leukocytes flows, and said second inflow passage is an inflow passage into which said second liquid including surfactant for dissolving cell membranes of said leukocytes and said fluorescent dyes for fluorescently staining said leukocytes flow.

12. The fluorescent particle counter according to claim 11, wherein said first inflow passage has a connecting portion capable of attaching a blood collecting unit or a blood bag.

13. The fluorescent particle counter according to claim 11, wherein a width $w_x$ of said fluorescent distribution measurement area in a portion departing from a wall by x meets the following expression if a rate of flow of liquid flowing in said outflow passage changes between a portion adjacent to said wall and a central portion of said outflow passage
width $w_x$ of said fluorescent distribution measurement area in said portion departing from said wall by x is equal to moving speed of said fluorescent particles in a point departing from said wall by x×time for said fluorescence measuring unit from obtaining one said stationary image till obtaining the next stationary image.

14. The fluorescent particle counter according to claim 13, wherein a side on an upstream side in said fluorescent distribution measurement area is a straight line intersecting said outflow passage, and a side on said downstream side in said area is a curved line projecting on said downstream side, and said area has a bullet-like shape.

15. The fluorescent particle counter according to claim 11, said counting unit counts any one of a fluorescent particle in a moment when passing through an edge on said upstream side in said fluorescent distribution measurement area and a fluorescent particle in a moment when passing through an edge on said downstream side in said fluorescent distribution measurement area in said stationary image, and does not count the other said fluorescent particle.

* * * * *